US007811313B2

United States Patent
Mon et al.

(10) Patent No.: US 7,811,313 B2
(45) Date of Patent: *Oct. 12, 2010

(54) DEVICE FOR TREATMENT OF TISSUE ADJACENT A BODILY CONDUIT BY THERMOCOMPRESSION

(75) Inventors: John Mon, Silver Spring, MD (US); Dennis Smith, Ellicott City, MD (US)

(73) Assignee: Boston Scientific Corporation, Natick, MA (US)

( * ) Notice: Subject to any disclaimer, the term of this patent is extended or adjusted under 35 U.S.C. 154(b) by 396 days.

This patent is subject to a terminal disclaimer.

(21) Appl. No.: 10/879,288

(22) Filed: Jun. 30, 2004

(65) Prior Publication Data

US 2004/0243199 A1    Dec. 2, 2004

Related U.S. Application Data

(63) Continuation of application No. 09/954,194, filed on Sep. 18, 2001, now Pat. No. 6,958,075.

(51) Int. Cl.
*A61F 7/00* (2006.01)
(52) U.S. Cl. ............... 607/96; 607/98; 607/101; 607/102; 607/104
(58) Field of Classification Search ............ 606/32, 606/33, 41–52; 607/96, 98–104
See application file for complete search history.

(56) References Cited

U.S. PATENT DOCUMENTS 3,125,096 A * 3/1964 Antiles et al. ............... 607/105

(Continued)

FOREIGN PATENT DOCUMENTS

WO    WO 93/08876 A1    5/1993

(Continued)

OTHER PUBLICATIONS

Prostatron, TUMT, Trans-Urethral Microwave Therapy, pp. 1-11.

(Continued)

*Primary Examiner*—Henry M Johnson, III
*Assistant Examiner*—Aaron Roane
(74) *Attorney, Agent, or Firm*—Brown Rudnick LLP

(57) ABSTRACT

A method and apparatus of treating tissue adjacent to a bodily conduit using thermotherapy, while preventing obstructions of the bodily conduit due to edema employs the circulation of warmed fluid to maintain the temperature of the bodily conduit walls and compresses the tissue to be treated to increase the effectiveness of the irradiated heat. An energy-emitting source containing catheter is inserted in a bodily conduit and is positioned in a region of the tissue to be treated so that the energy-emitting source radiates energy to the tissue to be treated. Fluid warmed to over 30° C. is circulated into and through the catheter to warm walls of the bodily conduit adjacent the catheter. The circulated fluid inflates a balloon to a pressure to compress the tissue to be treated. The combination of warmed fluid over 30° C. being circulated adjacent the bodily conduit to maintain the warmth in its walls and the compression of the tissue to be treated enables a natural stent to be formed that remains after the catheter and compression balloon is removed.

14 Claims, 5 Drawing Sheets

U.S. PATENT DOCUMENTS

| | | |
|---|---|---|
| 3,895,639 A | 7/1975 | Rodler |
| 4,589,423 A | 5/1986 | Turner |
| 4,709,698 A | 12/1987 | Johnston et al. |
| 4,754,752 A | 7/1988 | Ginsburg et al. |
| 4,799,479 A | 1/1989 | Spears |
| 4,813,429 A | 3/1989 | Eshel et al. |
| 4,955,377 A | 9/1990 | Lennox et al. |
| 4,998,933 A | 3/1991 | Eggers et al. |
| 5,007,437 A | 4/1991 | Sterzer |
| 5,019,075 A | 5/1991 | Spears et al. |
| 5,035,694 A | 7/1991 | Kasprzyk et al. |
| 5,061,267 A | 10/1991 | Zeiher |
| 5,114,423 A | 5/1992 | Kasprzyk et al. |
| 5,151,100 A | 9/1992 | Abele et al. |
| 5,190,540 A | 3/1993 | Lee |
| 5,191,883 A | 3/1993 | Lennox et al. |
| 5,226,430 A | 7/1993 | Spears et al. |
| 5,234,004 A | 8/1993 | Hascoet et al. |
| 5,251,645 A | 10/1993 | Fenn |
| 5,257,977 A * | 11/1993 | Eshel .................. 604/113 |
| 5,292,321 A | 3/1994 | Lee |
| 5,314,466 A | 5/1994 | Stern et al. |
| 5,330,518 A | 7/1994 | Neilson et al. |
| 5,344,398 A | 9/1994 | Hara |
| 5,368,591 A | 11/1994 | Lennox et al. |
| 5,370,608 A | 12/1994 | Sahota et al. |
| 5,413,588 A | 5/1995 | Rudie et al. |
| 5,417,653 A | 5/1995 | Sahota et al. |
| 5,417,689 A | 5/1995 | Fine |
| 5,431,648 A | 7/1995 | Lev |
| 5,441,532 A | 8/1995 | Fenn |
| 5,464,437 A | 11/1995 | Reid et al. |
| 5,464,445 A | 11/1995 | Rudie et al. |
| 5,480,417 A | 1/1996 | Hascoet et al. |
| 5,496,271 A * | 3/1996 | Burton et al. ............ 607/27 |
| 5,499,994 A | 3/1996 | Tihon et al. |
| 5,509,929 A | 4/1996 | Hascoet et al. |
| 5,520,684 A | 5/1996 | Imran |
| 5,540,655 A | 7/1996 | Edwards et al. |
| 5,540,679 A | 7/1996 | Fram et al. |
| 5,540,737 A | 7/1996 | Fenn |
| 5,545,137 A | 8/1996 | Rudie et al. |
| 5,549,559 A | 8/1996 | Eshel |
| 5,571,153 A | 11/1996 | Wallsten |
| 5,575,811 A | 11/1996 | Reid et al. |
| 5,578,008 A | 11/1996 | Hara |
| 5,620,480 A | 4/1997 | Rudie |
| 5,624,392 A | 4/1997 | Saab |
| 5,643,335 A | 7/1997 | Reid et al. |
| 5,653,692 A | 8/1997 | Masterson et al. |
| 5,688,269 A | 11/1997 | Newton et al. |
| 5,755,754 A | 5/1998 | Rudie et al. |
| 5,775,338 A | 7/1998 | Hastings |
| 5,810,888 A | 9/1998 | Fenn |
| 5,827,269 A | 10/1998 | Saadat |
| 5,843,144 A | 12/1998 | Rudie et al. |
| 5,879,347 A | 3/1999 | Saadat |
| 5,891,134 A | 4/1999 | Goble et al. |
| 5,902,268 A | 5/1999 | Saab |
| 5,916,240 A | 6/1999 | Rudie et al. |
| 5,916,241 A | 6/1999 | Rudie et al. |
| 5,931,860 A | 8/1999 | Reid et al. |
| 5,957,917 A | 9/1999 | Doiron et al. |
| 5,987,360 A | 11/1999 | McGrath et al. |
| 5,992,419 A | 11/1999 | Sterzer et al. |
| 6,102,929 A | 8/2000 | Conway et al. |
| 6,123,083 A | 9/2000 | McGrath et al. |
| 6,129,726 A | 10/2000 | Edwards et al. |
| 6,139,571 A | 10/2000 | Fuller et al. |
| 6,190,355 B1 | 2/2001 | Hastings |
| 6,200,598 B1 | 3/2001 | Needham |
| 6,224,590 B1 | 5/2001 | Daikuzono |
| 6,224,591 B1 | 5/2001 | Claren et al. |
| 6,245,062 B1 | 6/2001 | Berube et al. |
| RE37,315 E | 8/2001 | Lev |
| 6,366,818 B1 | 4/2002 | Bolmsjo |
| 6,433,147 B1 | 8/2002 | Ni et al. |
| 6,447,505 B2 * | 9/2002 | McGovern et al. ............ 606/41 |
| 6,477,426 B1 | 10/2002 | Fenn et al. |
| 6,524,274 B1 | 2/2003 | Rosenthal et al. |
| 6,540,771 B2 | 4/2003 | Dobak, III et al. |
| 6,567,705 B1 | 5/2003 | Stokes et al. |
| 6,617,864 B2 * | 9/2003 | Inoue et al. .................. 324/754 |
| 6,640,139 B1 * | 10/2003 | Ueberle ...................... 607/102 |
| 2001/0001314 A1 | 5/2001 | Davidson et al. |
| 2002/0151844 A1 | 10/2002 | Yang et al. |
| 2003/0055470 A1 | 3/2003 | Mon et al. |
| 2003/0069619 A1 | 4/2003 | Fenn et al. |

FOREIGN PATENT DOCUMENTS

| | | |
|---|---|---|
| WO | WO 93/09845 A1 | 5/1993 |
| WO | WO 99/07315 | 2/1999 |
| WO | WO 99/58194 A1 | 11/1999 |
| WO | WO 00/45758 | 8/2000 |

OTHER PUBLICATIONS

Gustavson, "The Chemistry and Reactivity of Collagen", Academic Press Inc., pp. 211-220, (1956).

Trembly et al., "Combined Microwave Heating And Surface Cooling of the Cornea", IEEE Transactions on Biomedical Engineering, vol. 38(1):85-91, (1991).

Agah et al., "Rate Process Model For Arterial Tissue Thermal Damage: Implications On Vessel Photocoagulation", Lasers In Surgery And Medicine, Wiley-Liss, Inc., vol. 15:176-184, (1994).

Surowiec et al., "Sar Characteristics of a Dual Intracavitary Applicator for Prostate Treatment", Hyperthermia Oncology 1992, vol. 1, p. 268, 1992.

Yeh et al., "Multiple Microwave Antenna System for Prostate Cancer Hyperthermia", Hyperthermia Oncology 1992, vol. 1, pp. 269, 1992.

Camart et al., "Rectal and Urethral Applicator Association for Prostatic Gland Microwave Thermotherapy: Modelling and Experimental Results", Hyperthermic Oncology 1996, vol. 2, pp. 598-600, 1996.

Brawer, "Prostate-Specific Antigen: Current Status", CA Cancer J. Clin. 1999, vol. 49, pp. 264-281, 1999.

Oesterling, "Prostate Specific Antigen: A Critical Assessment of the Most Useful Tumor Marker For Adenocarcinoma of the Prostate", The Journal of Urology, vol. 145, pp. 907-923, May 1991.

Zagars, M.D. et al., "The Prognostic Importance of Gleason Grade in Prostatic Adenocarcinoma: A Long-term Follow-up Study of 648 Patients Treated with Radiation Therapy", Int. J. Radiation Oncology Biol. Phys., vol. 31, No. 2, pp. 237-245, 1995.

Schröder et al., "Prostate Cancer Detection at Low Prostate Specific Antigen", J. Urol. 2000, vol. 163, p. 806, Mar. 2000.

Eschenbach, MD et al., American Cancer Society Guideline for the Early Detection of Prostate Cancer: Update 1997, CA Caner J. Clin. 1997, vol. 47, pp. 261-264.

Heynick, "Radiofrequency Electromagnetic Fields (RFEMF) and Cancer: A Comprehensive Review of the Literature Pertinent to Air Force Operations", Air Force Research Laboratory (AFSC) Human Effectiveness Directorate Directed Energy Bioeffects Division, Jun. 1999.

Field et al., "An Introduction to the Practical Aspects and Clinical Hyperthermia" Tayor & Francis, pp. 263, 290, 1990.

Fenn et al., "Minimally Invasive Molopole Phases Arrays For Hyperthermia Treatment Of Breast Carcinomas: Design And Phantom Tests", Presented at the 1994 International Symposium of Eclectromagnetic Compatibility, pp. 566-569, May 17-19, 1994.

Vitrogan, "Elements on Electric and Magnetic Circuits", Rinehart Press, pp. 31-34, 1971.

England et al., "Dielectric Properties of the Human Body in the Microwave Region of the Spectrum", Nature, vol. 163, pp. 487-488, Mar. 26, 1949.

Duck, "Physical Properties of Tissue, A Comprehensive Reference Book", Academic Press Inc., San Diego, CA, pp. 320-321, 1990.

Foster et al., "Dielectric Properties of Tumor and Normal Tissues at Radio through Microwave Frequencies", Journal of Microwave Power, 16 (2), pp. 107-119, 1981.

Valdagni, M.D. et al., "Report of Long-term Follow-up in a Randomized Trial Comparing Radiation Therapy and Radiation Therapy Plus Hyperthermia to Metastatic Lymphnodes in Stage IV Head and Neck Patients", Int. J. Radiation Oncology Biol Phys., vol. 28, No. 1, pp. 163-169, 1993.

Overgaard et al., "Hyperthermia as an Adjuvant to Radiation Therapy of Recurrent or Metastatic Malignant Melanoma. A Multicentre Randomized Trial by the European Society for Hyperthermic Oncology", Int. J. Hyperthermia, vol. 12, No. 1, pp. 3-20, 1996.

Hall, "Radiobiology for the Radiologist", J.B. Lippincott Company, Philadelphia, pp. 262-263, 1994.

Perez et al., "Principles and Practice of Radiation Onocology", J.B. Lippincott Company, Philadelphia, second edition, pp. 396-397, 1994.

Sapareto et al., "Thermal Dose Determination in Cancer Therapy", Int. J. Radiation Oncology Biol. Phys., vol. 10, No. 6, pp. 787-800, Jun. 1984.

von Hippel et al., "Dielectric Analysis of Biomaterials", Massachusetts Institute of Technology, pp. ai-ii, and 1-20, Oct. 1973.

Bassen et al., "Evaluation of an Implantable Electric-Field Probe within Finite Simulated Tissues", American Geophysical Union, vol. 12, No. 6(s), pp. 15-25, Nov.-Dec. 1977.

Samaras et al., "Production of Controlled Hyperthermal Fields for Cancer Therapy", Urban & Schwarzenberg, pp. 131-133, 1978.

Gentili et al., "Two-Element Radiating System for Endocavitary Hypertermia", Hyperthermic Oncology 1988, vol. 1, pp. 904-905, Aug. 29-Sep. 1988.

Barry et al., "The American Urological Association Symptom Index for Benign Prostatic Hyperplasia", vol. 148, pp. 1549-1557, Nov. 1992.

Vernon et al., "Radiotherapy with or without Hyperthermia in the Treatment of Superficial Localized Breast Cancer: Results from Five Randomized Controlled Trials", Int. J. Radiation Oncology Biol. Phys., vol. 35, No. 4, pp. 731-744, 1996.

Office Action dated Jul. 17, 2007 for U.S. Appl. No. 10/436,500, filed May 13, 2003.

* cited by examiner

DEVICE FOR TREATMENT OF TISSUE ADJACENT A BODILY CONDUIT BY THERMOCOMPRESSION

CROSS REFERENCE TO RELATED APPLICATIONS

This application is a continuation application of application Ser. No. 09/954,194 filed Sep. 18, 2001, issued as U.S. Pat. No. 6,958,075. The disclosure of the above-referenced patent applications, as well as that of each US and foreign patent and patent application identified in the specification of the present application, is incorporated herein by reference.

BACKGROUND OF THE INVENTION

1. Field of the Invention

The present invention generally relates to a system and method for administering focused energy to a body using either a single energy applicator or multiple microwave applicators, warmed fluid and compression in order to treat visible tumors and microscopic malignant and benign cells in tissue with thermotherapy. In particular, the present invention relates to a transurethral catheter for microwave thermal and warming therapy with compression of prostate tissue adjacent a urethra to create a biological stent.

2. Description of the Prior Art

In order to treat the prostate with thermotherapy, it is necessary to heat a significant portion of the prostate gland while sparing healthy tissues in the prostate as well as the surrounding tissues including the urethral and rectal walls of a patient. The prostate gland encircles the urethra immediately below the bladder. The prostate, which is the most frequently diseased of all internal organs, is the site of a common affliction among older men, benign prostatic hyperplasia (BPH), acute prostatitis, as well as a more serious affliction, cancer. BPH is a nonmalignant, bilateral nodular tumorous expansion of prostate tissue occurring mainly in the transition zone of the prostate. Left untreated, BPH causes obstruction of the urethra that usually results in increased urinary frequency, urgency, incontinence, nocturia and slow or interrupted urinary stream.

Recent treatment of BPH includes transurethral microwave thermotherapy in which microwave energy is employed to elevate the temperature of tissue surrounding the prostatic urethra above about 45° C., thereby thermally damaging the tumorous prostate tissue. U.S. Pat. Nos. 5,330,518 and 5,843,144 describe methods of ablating prostate tumorous tissue by transurethral thermotherapy, the subject matter of which incorporated by reference. However, improvements still need to be made in this type of therapy to further maintain or enhance the patency of the urethra after the thermotherapy treatment. In particular, urine flow is not always improved despite ablation of the tumorous tissue causing constriction of the urethra because edema produced by the transurethral thermo-therapy treatment blocks the urethra passage resulting in patients treated by the above methods to be fitted with catheters for several days or weeks after the thermotherapy treatment.

U.S. Pat. Nos. 5,007,437, 5,496,271 and 6,123,083 disclose transurethral catheters with a cooling balloon in addition to the anchoring or Foley balloon and are incorporated by reference herein. However, these patents circulate fluid, which acts as a coolant for removing heat preferentially from the non-prostatic tissue adjacent thereto, through the cooling balloons. The '083 patent further discloses the use of a thermotherapy catheter system taught by U.S. Pat. No. 5,413,588 that employs chilled water between about 12°-15° C. as the coolant. Chilled water significantly cools the urethra adjacent the cooling balloon. Likewise, the '271 patent describes a coolant as the fluid to keep the urethral wall temperatures cool. This chilling of the urethra does not aid in maintaining an opening within the heated urethra after the cooling balloon is removed, and reduces the therapeutic effect in the tissue immediately adjacent the urethral wall.

Another known alternative to thermal surgery, as described in U.S. Pat. No. 5,499,994, is to insert a dilation balloon in the urethra and to expand the dilation balloon to compress the obstructed urethra. However, the expansion of the dilation balloon occurs over 24 hours and the patient still is not cured of the diseased prostate and can cause adverse effects (e.g., tearing of the urethral walls). U.S. Pat. No. 6,102,929 describes a post-operative procedure where the prostate tissue is expanded after the surgical procedure to enlarge the urethra to enable a patient to void comfortably. This expansion requires insertion of another device and requires the device to remain in the patient for a day or more.

In view of the fact that post-treatment catheters or other devices are still considered necessary by the medical community, further improvements are needed in thermotherapy to avoid the obstruction caused by edema and to maintain and enhance the opening of the urethra.

SUMMARY OF THE INVENTION

The present invention is directed to a device and a method for thermally treating tissue adjacent a bodily conduit, such as a urethra, while preventing obstructions of the bodily conduit due to edema. To achieve this object, the instant invention employs a catheter with an energy-emitting source and a compression balloon surrounding the energy-emitting source through which a warmed fluid flows to warm the bodily conduit walls adjacent the compression balloon.

While the instant invention will be described with respect to a preferred embodiment where the bodily conduit is the urethra and prostatic tissue is to be treated by thermotherapy, the combination of warmed fluid, compression and microwaves can be used to achieve the above goal in other bodily conduits including, but not limited to, cardiovascular, esophageal, nasal pharynx, and rectal cavities. That is, it is a goal of the instant invention to open up bodily conduits so that the normal function of that conduit is not hampered. The power to the energy-emitting source and diameters and shaping of the compression balloon and catheter will vary depending upon the tissue or bodily conduit to be treated.

Unlike known techniques that circulate a coolant to cool the urethral walls, the instant invention circulates a warmed fluid to maintain the temperature of the urethra above 30° C. Applicants recognized that a biological stent or molded opening was not able to be formed with cooled circulation fluid (i.e., fluid circulated into a patient in the range of 25° C.-30° C.). A preferred range of temperature for the warmed fluid would be between 30° to 60° C. A preferred example would be to circulate fluid into a patient at 35° C. Applicants have formed a biological stent when the external temperature of the warmed fluid before circulation through a patient measures 33° C.

According to the invention, a select volume of collagen-containing tissue surrounding the urethra is heated to a temperature greater than about 43° C. for time sufficient to substantially destroy the select volume of tissue. Prior to energizing the energy-emitting source, the preshaped compression balloon is filled with the warmed fluid to expand the urethral walls compressing the prostate thereby reducing blood flow in the prostate surrounding the urethral walls so that the energy-absorptive heating is more efficient in the region of constricted blood supply. As a result, the proteins of the urethral walls become denatured or are unraveled in the presence of the heat emitted from the energy-emitting source. The warmed fluid, which expands the compression balloon, supports the denaturing process while preventing the absorbed, energy-emitted heat from burning the urethral walls. This denaturing allows the urethral walls to conform to the expanded shape of the urethra created by the compression balloon and reduces the elasticity of the urethral walls so that a stent reinforcement period following the heating naturally solidifies the expanded shape resulting in a biological stent. That is, the expanded bodily conduit walls do not return to their previous shape after the compression balloon is deflated and removed thereby achieving a natural opening in the a bodily conduit, such as a urethra.

According to a preferred embodiment of the invention, a stent reinforcement period of approximately 10 minutes or less follows the heating step. The stent reinforcement period maintains the pressure of the compression balloon after power to the energy-emitting source has been turned off so that a solidified expanded urethra is achieved minutes after thermotherapy and a catheter or other device is not necessary.

The compression balloon is generally cylindrical with a sloped area on both sides of the compression balloon and is symmetrical along the length of the diameter according to a preferred embodiment. The position of the energy-emitting source in the preferred embodiment may be fixed. However, the compression balloon may be of any shape to create a desired mold or stent within a bodily conduit or urethra and may be asymmetrical along the length of the catheter.

The compression balloon needs to maintain about 10-25 psi against the urethral wall along the length of the catheter with the preferred level of pressure being about 15 psi. The compression balloon may have a variable diameter along the length of the catheter. Alternatively, the compression balloon may be a single balloon or multiple balloons.

In one embodiment, the diameter of the compression balloon varies across the radius to achieve an asymmetric molding of the bodily conduit. Alternative shapes of the compression balloon would include cone-shaped cylinders where the apex is adjacent the bladder neck or directed away from the bladder neck depending on the desired biological stent. These cone-shaped cylinders would enable the energy-emitted heat to focus on a particular area surrounding the bodily conduit, as well as create a biological stent or opening corresponding to this shape.

According to the invention, the warmed fluid is circulated through the compression balloon in conjunction with an outflow restriction so that the pressure of flow in the balloon is maintained at about 10-25 psi. The positioning of the inlet and outlet orifices in the compression balloon enables laminar flow within the compression balloon. Further, the inlet and outlet orifices in the compression balloon are arranged as to minimize air pockets in the balloon and thus, "hot spots" which occur as a result of the air pockets.

In addition to the various shapes of the compression balloon, the compression balloon could be partially covered with a grounded or ungrounded conductive material that shields or absorbs the energy-emitting rays so that the heat could be reduced at some portions of the prostatic tissue and focussed at other portions. In this embodiment, the energy-emitting source or microwave antenna may be movable so that the position of its energy-emitting portion can vary to optimize the heating of tissue for a particular therapy. The preferred location and movement, if any, of the energy-emitting source would depend on the size, shape and the shielding of the compression balloon.

BRIEF DESCRIPTION OF THE DRAWINGS

These and other features and advantages of the invention will be further understood from the following detailed description of the preferred embodiment with reference to the accompanying drawings in which.

DETAILED DESCRIPTION OF THE PREFERRED EMBODIMENTS

The present invention is directed to a device and a method for thermally treating tissue adjacent a bodily conduit, such as a urethra, while preventing obstructions of the bodily conduit due to edema. Examples and alternatives of the method and apparatus according to the present invention will be described and illustrated below after a brief discussion of collagen.

Collagen is a principal component of connective tissue and fibromuscular tissues. Collagen also has known properties such as plastic remodeling when subjected to high temperatures (e.g. about 60° C. to 70° C.). Specific remodeling temperatures are generally more exactly identifiable for a type and age of tissue in a particular location of the body. In the embodiment according to the invention, Applicants theorize that the remodeling temperature is lowered as a result of the bodily conduit being reshaped and the tissue adjacent to the conduit being compressed to significantly reduce the blood flow. General principles of collagen and collagen reactivity to thermal treatment are known in the art and are described in the following articles, amongst others: Gustavson, The Chemistry and Reactivity of Collagen, Academic Press, Inc., New York, 1956, specifically including p.p. 211-220; Agah et. al., Rate Process Model For Arferial Tissue Thermal Damage: Implications on Vessel Photocoagulation, Lasers in Surgery and Medicine, 15:176-184 (1994); Trembly et. al., Combined Microwave Heating and Surface Cooling of the Cornea, IEEE Transactions On Biomedical Engineering, Vol. 38, No. 1, 1991, Stringer et. al., Shrinkage Temperature of Eye Collagen, Nature, No. 4965, pp. 1307.

Of specific interest, collagen is found in fibromuscular tissue and other interstitial connective tissue forming part of or surrounding various ducts in the body. For example, the urethra is a duct in the lower urinary tract that passes fluid from the bladder, through the prostate, and out of the body via the penis. Proximal portions of the prostatic urethra are surrounded by a ring of fibromuscular tissue and by interstitial tissue in the prostate, both types of tissue including collagen. Manipulation of this collagen in the method of the present invention is used to remedy various dysfunctions of the prostate and/or urethra, such as benign prostatic hyperplasia. Accordingly, the urethra is one example of a duct in the body having collagen rich surrounding tissue and a diameter that must be carefully controlled to maintain normal function, which is addressed by the method of the present invention.

Figure 1:
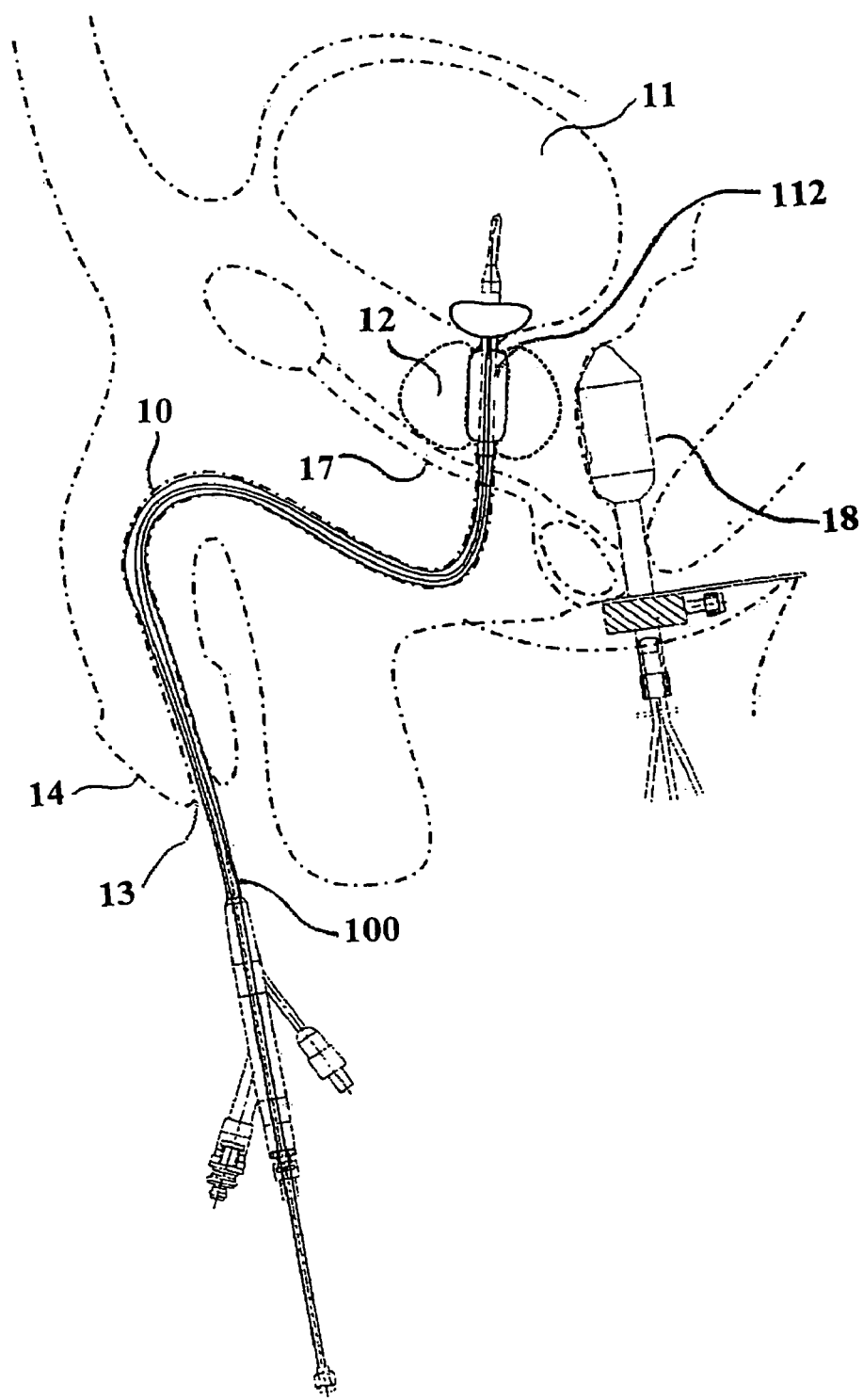
FIG. 1 is a vertical sectional view of a male pelvic region showing urinary organs affected by benign prostatic hyperplasia and an inserted catheter according to the invention with inflated compression and Foley balloons.

A first method and apparatus of maintaining or expanding the diameter of the urethra into a selected urethral shape after microwave thermotherapy treatment for benign prostatic hyperplasia to restore patency to the urethra is illustrated in FIGS. 1-6. FIG. 1 is a. vertical sectional view of a male pelvic region showing the effect of benign prostatic hyperplasia (BPH) on the urinary organs. Urethra 10 is a duct leading from bladder 11, through prostate 12 and out orifice 13 of penis end 14. Benign tumorous tissue growth within prostate 12 around urethra 10 causes constriction of urethra 10, which interrupts the flow of urine from bladder 11 to orifice 13. The tumorous tissue of prostate 12, which encroaches urethra 10 and causes the constriction (not shown, as compression balloon 112 is inflated),. can be effectively removed by heating and necrosing the encroaching tumorous tissue. Ideally, with the present invention, periurethral tumorous tissue of prostate 12 anterior and lateral to urethra 10 is heated and necrosed while avoiding unnecessary and undesirous damage to urethra 10 and to adjacent healthy tissues, such as external sphincter 17, rectum 18, and bladder neck 19.

Figure 2:
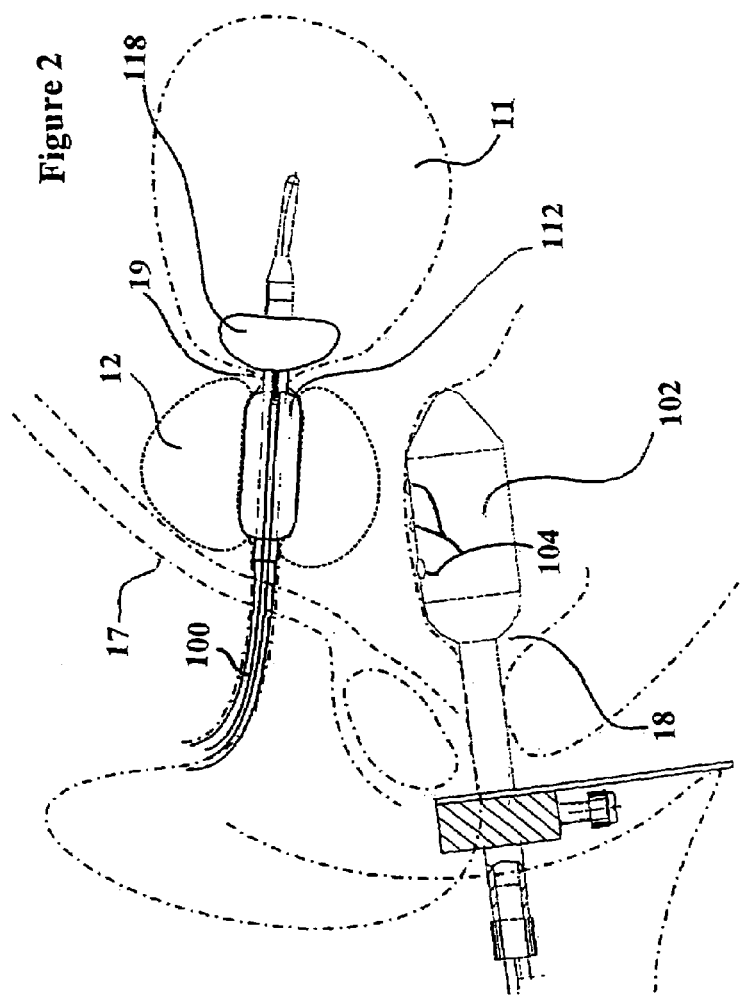
FIG. 2 is an enlarged portion of FIG. 1.

FIG. 2 is an enlarged sectional view of FIG. 1 illustrating specific anatomical features including urethra 10 and bladder 11 and showing a catheter 100 according to the invention with an inflated compression balloon 112 and an inflated Foley or anchoring balloon 118. As shown on FIGS. 14, the instant invention employs a catheter 100 with an energy-emitting source 110 and a compression balloon 112 surrounding the energy-emitting portion of source 110 through which a warmed fluid flows to warm the urethra walls adjacent the compression balloon. A selective heating of benign tumorous tissue in prostate 12 (transurethral thermotherapy) is made possible by energy-emitting-containing catheter 100 of the present invention. A rectal probe 102 with a number of sensors is inserted into rectum 18 and measures the amount of heat generated by the absorbed emitted energy at the rectal wall.

As shown in FIG. 2, three sensors 104 are mounted on probe 102. The sensors are preferably integrally mounted at differing radial locations on the probe and spaced approximately 1 centimeter from one another. Foley balloon 118 is inserted into a patient's bladder so that the proximal end of the compression balloon is located at the patient's prostate immediately distal of the bladder neck. The length of compression balloon 112 varies depending upon the size of a patient's bladder. A typical length of the compression balloon would be about 40 millimeters and the length can range from 25 to 60 millimeters.

Catheter 100 would be around 18 French (French is a measurement equal to 0.333 mm or 0.013 inch). Since the average diameter of a male adult human is about 22 French, the deflated compression balloon 112 that surrounds the catheter would add approximately 2 French so that diameter of catheter 100 and balloon 112 would be less than that of the patient's urethra for ease of insertion and less pain for the patient. Multi-Lumen Shaft 100 and associated molded parts are preferably extruded of a medical grade polymer sold by Concept Polymer Incorporated under the trademark C-Flex™. The compression balloon is preferably molded from a medical grade polyester material sold by Allied under the trademark PET™, that has a limit of stretch based on its initial maximum molded shape. Alternative materials can include a silicone material manufactured by Dow Corning Inc. under the trade name Silastic R™ type Q7-4850 and type Q7-4765, for the shaft extrusion and the molded manifold, and Elastosil type LR3003/30Us for the anchoring balloon 118. The material of catheter 100 preferably has a Shore D hardness between 50 D and 80 D.

After full insertion (i.e., the deflated Foley balloon reaching into the patient's bladder), a fluid (sterile water) is pumped through the Foley inflation valve 113 thereby to inflate Foley balloon 118 and hold the catheter within the patient's urethra. Inflation valve 113 maintains fluid in the Foley balloon with the desired pressure so that the catheter is anchored in the patient. However, the catheter is still capable of limited longitudinal movement with respect to the urethra. After Foley balloon 118 has been inflated, a warmed fluid, preferably a low-loss liquid (e.g., deionized or sterile water), is slowly pumped through the one or more catheter inflation/circulation lumens 120 (FIG. 3a) into the prostate compression balloon 112 to inflate the same expanding the urethral walls and maintaining the temperature of the urethral walls above 30° C. The diameter of the inflated compression balloon would be approximately in the range of 25-60 French. The warmed fluid used to inflate compression balloon 112 is preferably a minimally energy absorptive solution which conducts microwaves to the tissue to be heated more efficiently.

Figure 3A:
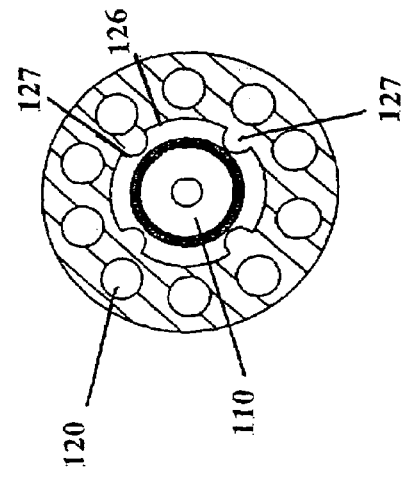
FIG. 3a is a cross-sectional view of the urethral catheter of FIG. 3 taken along line a-a.
Figure 3:
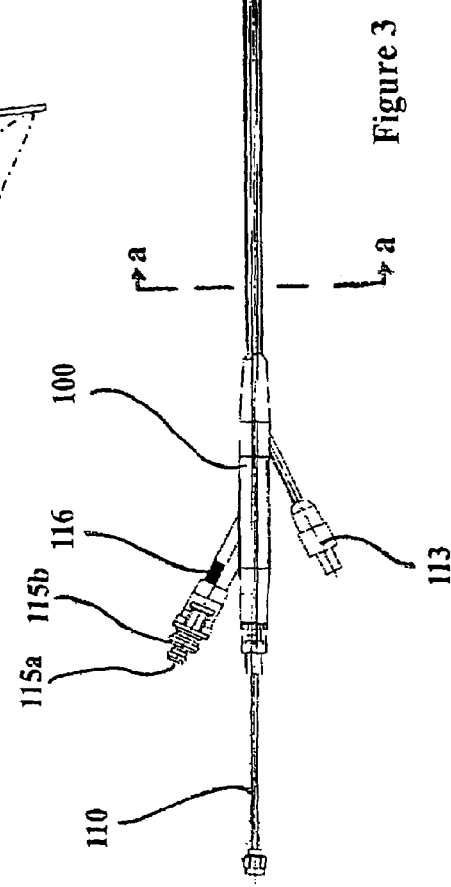
FIG. 3 is a plan view of the urethral catheter of the present invention.

A typical implementation of a catheter according to the invention is shown in FIG. 3. Foley balloon 118 is deflated in this Figure. As shown on the left-hand side of the Figure, a Foley inflation valve 113, a warmed, sterile-fluid intake 115a and a sterile-fluid outtake 115b are provided to receive fluid. The sterile-fluid intake and outtake 115a, 115b enable the circulation of sterile fluid in the compression balloon during thermotherapy and maintain the desired pressure to achieve the specific fluid flow pattern and distribution of fluid within the balloon. A central lumen 126 receives the energy-emitting source 110, which may be an antenna in the form of a coaxial cable. As shown in FIG. 3a, protrusions 127 are formed in central channel 126 in order to keep energy-emitting source 110 centralized inside catheter 100 and to create channels for the outtake fluid flow. Protrusions 127 enable the distance between the energy-emitting source and outside wall of the catheter to remain constant thereby ensuring a consistent heating pattern at the energy-emitting portion of the source 110. The energy emitting source 110 is directed coupled to the low-loss fluid to maximize emitted power and to cool the shaft of the energy-emitted source.

Figure 3B:
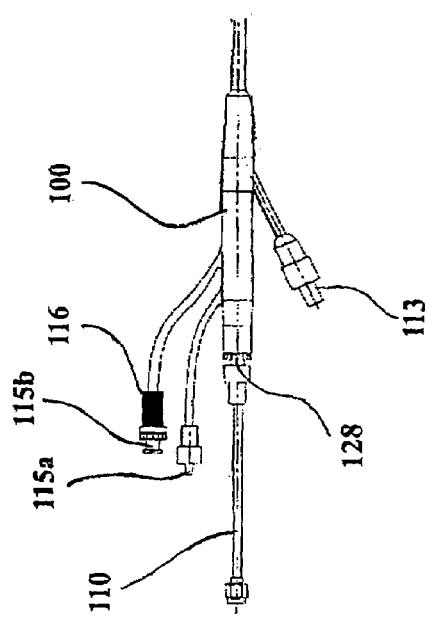
FIG. 3b shows an alternative embodiment of the warmed fluid pumping system.
Figure 4:
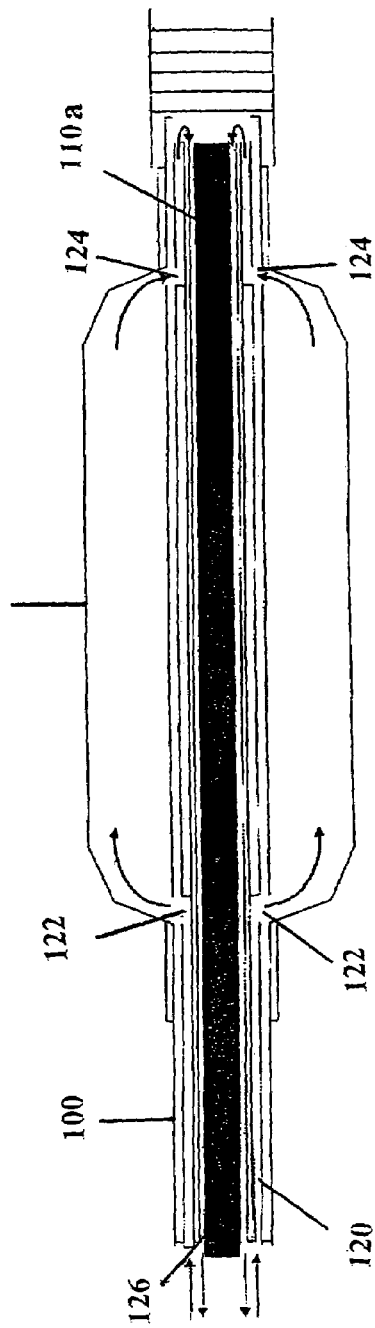
FIG. 4 illustrates the fluid flow through the catheter for inflation of the compression balloon.

As shown in FIG. 4, orifices 122, 124 are employed in one or more of catheter lumens 120 on both sides of compression balloon 112 so that warmed fluid can be pumped through lumens 120 into compression balloon 112 at one end and out at the other end. The warmed water is then circulated through central orifice 126, which holds an energy-emitting source 110, such as a microwave antenna, and flows out of catheter 100 external of a patient. The placement and diameter of the orifices 122, 124 enables sufficient fluid flow and pressure of about 10-25 psi to be maintained in compression balloon 112 during the entire thermotherapy treatment. In the preferred embodiment, an outtake-fluid-side channel is fitted with a restrictive orifice 116 to limit the compression balloon pressure for maximum fluid flow through compression balloon 112. The restrictive orifice 116, in an alternative embodiment, can be located immediately external to the catheter in the connective tubing (e.g., 115a, 115b) used to connect the catheter to the external fluid warming pumping system (FIG. 3b). The pressurized circulation of the warmed fluid is such that air pockets are reduced in the inflated balloon. Accordingly, air pockets in the compression balloon, which may result in "hot spots" causing burns on the urethral walls, are avoided. This results in the desired compression of the prostatic urethral tissue, without burning the urethral walls, which is maintained during and after the thermotherapy treatment.

It is desired to heat the diseased prostate tissue to a therapeutic temperature (greater than about 43° C.) while maintaining the temperature of the non-prostate tissue lining the urethra above 30° C. The non-prostate tissue includes the urethral wall and adjacent tissue and is disposed between the energy-emitting source 110 and prostatic tissue 12. The energy-emitting portion 110a of source 110 is disposed in catheter 100 so that it rests within the compression balloon 112. Energy-emitting portion 110a preferably emits an irradiating microwave field, which varies as an inverse function (e.g., inverse square) of the distance between the energy-emitting portion 110a (e.g., microwave antenna) and the tissue to be heated. Consequently, the non-prostate tissue of urethral wall 10, which is closer to energy-emitting portion 110a than prostatic tissue 12, would be heated to a higher temperature than the prostatic tissue to be treated. Likewise, proximate prostate tissue would be heated to a higher temperature than more distal prostate tissue.

U.S. Pat. No. 5,007,437 to Sterzer discloses the use of a balloon to compress the prostate tissue and to move the urethral wall away from the microwave antenna, which produces the heat. This method reduced the microwave field intensity and the resultant heat produced at the urethral wall by moving the urethral wall further from the heat-producing antenna. However, Sterzer also employed a circulating fluid to continuously cool the urethral wall while the urethral wall was inflated. Applicants recognized that this circulating coolant was preventing the urethral wall and adjacent prostatic tissue from reaching a temperature sufficient to denature the protein or enable plastic remodeling. As a result, Applicants theorized that the use of an inflated prostate compression balloon together with the circulation of warmed fluid would mitigate the denaturing problem, as shown in FIGS. 5a and 5b.

Figure 5A:
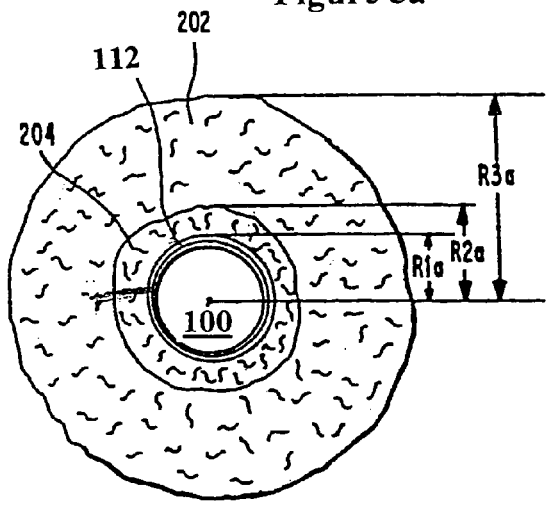
FIGS. 5a and 5b are schematic, cross-sectional views of a urethra showing the compression balloon in the uninflated and inflated states, respectively to illustrate the expansion of the urethral walls and prostate according to the invention.
Figure 5B:
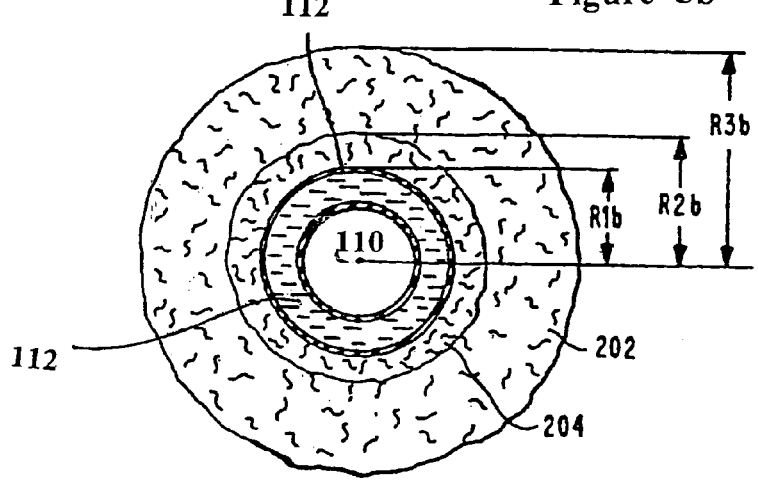

FIGS. 5a and 5b respectively show a cross-section of a deflated compression balloon and a cross-section of an inflated compression balloon. The radial distances from energy-emitting source or microwave antenna 110 to distal prostatic tissue 202 and proximal tissue 204, which includes the urethral wall and adjacent non-prostatic tissue, when compression balloon 112 is deflated are smaller than those distances are when compression balloon 112 is inflated. As shown, inflated compression balloon 112 forms a symmetrical toroid extending. around the entire circumference of the urethral catheter. Specifically, the radial distance $R_{1b}$ from microwave antenna 110 to the inner circumference of proximal tissue 204 with inflated compression balloon 112 is significantly larger than the corresponding radial distance $R_{1a}$ with deflated compression balloon 112. Similarly, the radius $R_{2b}$ to the inner circumference of prostate tissue 202 with inflated compression balloon 112 is significantly larger than the corresponding radial distance $R_{2a}$ with deflated compression balloon 112. Because prostate tissue is soft and compressible, the difference between the outer and inner radii $R_{3b}$ and $R_{2b}$ of prostate tissue 202 with inflated compression balloon 112 is substantially reduced with respect to the corresponding difference between radii $R_{3a}$ and $R_{2a}$ with deflated compression balloon 112.

Consequently, the inflated compression balloon causes the prostate 12 to be compressed from the urethral wall thereby decreasing the thickness of the tissue between the compressed wall of the urethra and the margins of the prostate capsule. The tissue more distal 202 is not as compressed as the tissue more proximal to the urethra 204. Since the actual tissue thickness through which the energy emitted by the antenna 110 is less, the energy deposited is more evenly distributed throughout the entire prostate capsule. This makes it possible to heat the prostatic tissue more evenly and to higher therapeutic temperatures without heating any part of the non-prostatic tissue beyond its maximum safe temperature.

At the same time the inflated compression balloon 112 constricts the blood flow in the compressed prostate so that the irradiated heat is not carried away by the natural blood flow and thus makes this tissue more susceptible to heating by the emitted energy. Since the overall tissue thickness is reduced the amount of energy required to effectively heat the prostate tissue 204 to a therapeutic temperature is reduced. Conversely, in typical non-compressed therapies, the amount of energy required to raise the temperature of the more distal prostatic tissue 202, that may be adjacent to the rectal wall to a maximize safe temperature of 41° C. will be significantly higher that than required according to the invention. Thus, it is possible to heat the prostatic tissue more evenly and to higher temperatures without heating any part of the non-prostatic tissue beyond its safe maximum temperature.

In order to heat proximal tissue 204 above a predetermined collagen transition temperature during a microwave thermotherapy treatment, warmed fluid above 30° C., preferably in the range of about 31° C.-60° C., is circulated through compression balloon 112, in contrast to a coolant. As a result, the urethral wall and adjacent tissue is sufficiently denatured so that a natural biological stent can be formed after the thermotherapy treatment.

The warming of the urethral wall above 30° C. and maintaining of this temperature serves to denature the proteins of the urethral wall; but does not heat the urethral wall beyond a maximum safe temperature. This denaturing allows the urethral walls to conform to the expanded shape of the urethra created by compression balloon 112 and reduces the elasticity of the urethral walls so that a stent reinforcement period following the heating of the thermotherapy treatment naturally solidifies the expanded shape resulting in a biological stent. That is, the expanded urethral walls do not return to their previous shape after the compression balloon is deflated and removed thereby achieving a natural opening in the a bodily conduit, such as a urethra.

The stent reinforcement period that follows the termination of the heating of the prostatic tissue requires that the compression balloon remain inflated at the desired pressure of 10-25 psi for less than about 10 minutes. During this reinforcement period, fluid typically no longer needs to be circulated through the compression balloon as only the maintaining of the pressure in the compression balloon serves to solidify the biological stent. That is, The stent reinforcement period maintains the pressure of the compression balloon after power to the energy-emitting source has been turned off so that a solidified expanded urethra is achieved minutes after thermotherapy and a urine drainage catheter or other device is not necessary.

Figure 6:
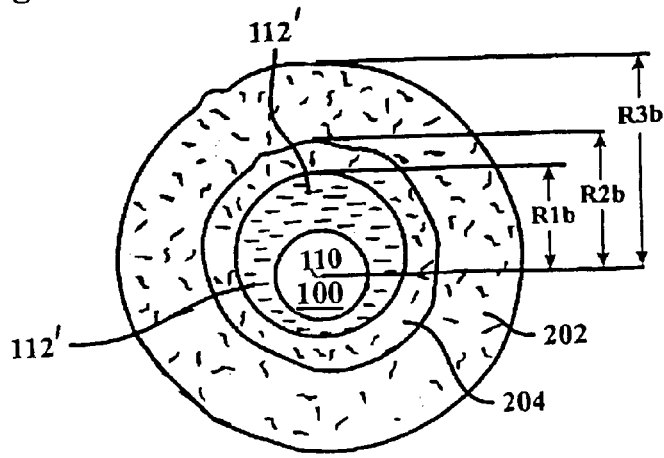
FIG. 6 is a schematic cross-sectional view of the urethra illustrating an inflated, asymmetric compression balloon according to the invention.

Compression balloon 112 is generally cylindrical with a sloped area on both sides of the compression balloon and is symmetrical along the length of the diameter according to a preferred embodiment. However, compression balloon 112 may be of any shape to create a desired mold or stent within a bodily conduit or urethra. As shown in FIG. 6, the compression balloon 112' on catheter 100 is designed so that it inflates asymmetrically around catheter 100. The asymmetrical balloon 112' inflates a bodily conduit so that a region of tissue adjacent the bodily conduit receives more or less radiate energy from the energy-emitting source 110 depending upon the width of the inflated compression balloon 112'. The wider the inflated compression balloon, the more compressed the tissue adjacent the bodily conduit and the further from the heat producing source.

Compression balloon 112 needs to maintain about 10-25 psi against the urethral wall along the length of the catheter with the preferred level of pressure being about 15 psi. The compression balloon may have a variable diameter along the length of the catheter, as shown in FIGS. 7a-7d. Alternatively, the compression balloon may be a single balloon or multiple balloons.

Figure 7A:
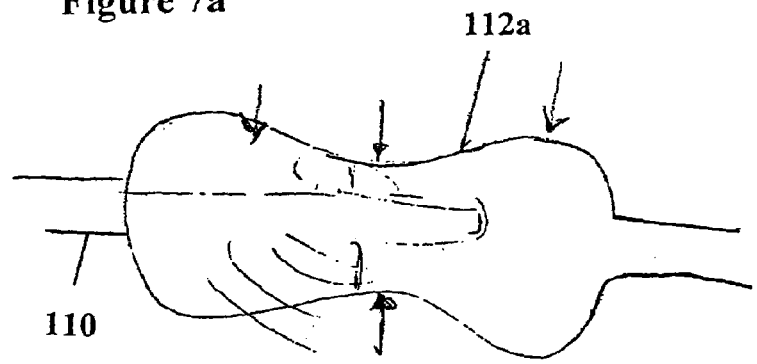
FIGS. 7a-d illustrate alternative compression balloon shapes and techniques for additional shielding implementations.
Figure 7B:
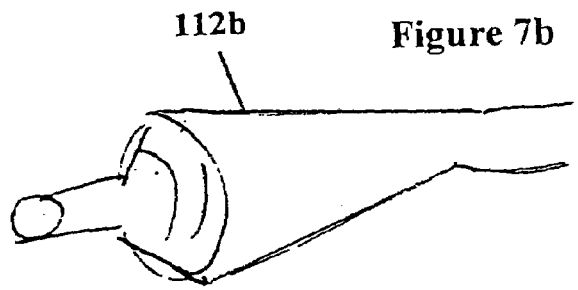
Figure 7C:
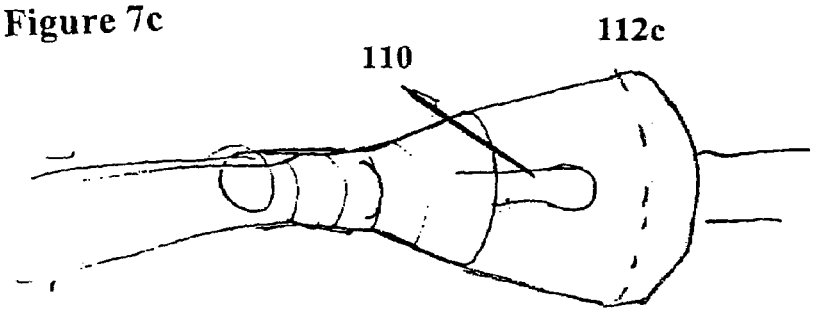
Figure 7D:
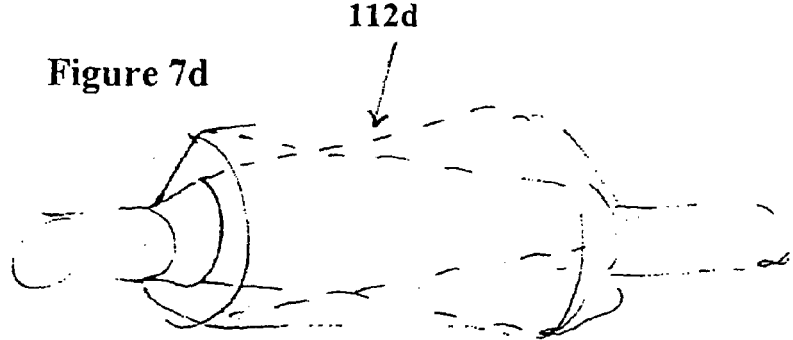

In one embodiment, the diameter of the compression balloon varies across the radius to achieve an asymmetric molding of the bodily conduit. This shape is shown in FIG. 7a where the compression balloon only expands to about 27 French in the middle and 46 F on either end. Alternative shapes of the compression balloon would include cone-shaped cylinders (FIGS. 7b-c) where the apex is adjacent the bladder neck or directed away from the bladder neck depending on the desired biological stent. These cone-shaped cylinders would enable the energy-emitted to be selectively focussed on a particular area surrounding the bodily conduit, as well as create a biological stent or opening corresponding to this shape. Alternatively, the cone-shaped or other desired shaped balloons may provide preferentially localized therapy for a non-specific disease.

In addition to the various shapes of the compression balloon, the compression balloon could be covered with a material that shields the energy-emitting rays so that the heat could be reduced at some portions of the prostatic tissue and focused at other portions. That is, the shielding would enable preferential heating of prostatic tissue. In this embodiment, the effective heating area of the catheter/balloon/antenna combination is controlled by a selective addition of distally located shielding material provided along the shaft of the catheter either internally or externally applied. Alternatively or in addition to the catheter shielding material, shielding material may be applied on a surface of the compression balloon, either internally or externally. According to another embodiment of the instant invention, a metallic coating may be applied on at least one of the catheter shaft and compression balloon. The metallic coating may not be connected to ground in order to reflect or distribute emitted energy thereby preferentially heating the tissue to be treated.

The applied shielding when grounded selectively absorbs microwave energy emitted from the energy-emitting source or antenna to modify the heating pattern and to control the deposition of heat into the surrounding target tissue. To electrically ground the shield, internally connected lead wires are passed through the fluid circulation lumens or embedded in the catheter shaft material and are connected to the most distal end of the catheter. These wires are then terminated to the external electrical surface of the energy-emitting source and/ or terminated separately to a system grounding point for the adequate dissipation of the absorbed emitted energy. In an exemplary embodiment, the lead wires or electrical conductors may be grounded to an external antenna. The electrical conductors may be made of one of a metallic film, metallic foil and metallic wire mesh, which are integrated into at least one of the catheter shaft 100 and the compression balloon 112, and are applied at multiple locations at a distance distal of the energy-emitting source 110 to produce the desired heating pattern. The amount and location of shielding provided on either the catheter shaft and/or the compression balloon is variable depending upon the desired heating pattern.

In this embodiment, the energy-emitting source 110 or microwave antenna may be movable so that the position of its energy-emitting portion 110a can vary to optimize the heating of tissue for a particular therapy. As shown in FIG. 3b, a longitudinal antenna locator device 128 would be able to move the antenna and lock the same into the desired position. The preferred location and movement, if any, of the energy-emitting source would depend on the size, shape and the shielding of the compression balloon.

Accordingly, the method and apparatus of the present invention ablate the diseased tissue causing an obstruction in the bodily conduit, while forming a natural or biological stent in the bodily conduit so edema or swelling does not close the bodily conduit. As a result, an unobstructed opening in a bodily conduit, such as the urethra, is formed after the stent reinforcement period.

Moreover, the circulation of warmed fluid, expansion and heating according to the invention effectively plastically remodels the collagen rich surrounding tissue into a selected shape having a desired expanded diameter. Thus, the instant invention can increase the patency of the prostatic urethra and surrounding tissue by increasing a urethral diameter.

Although the present invention has been described with reference to preferred embodiments, workers skilled in the art will recognize that changes may be made in form and detail without departing from the spirit and scope of the invention.

We claim:

1. An apparatus for treatment of tissue within a body requiring thermotherapy, said apparatus comprising:
   a) a catheter to be inserted into a bodily conduit, the catheter defines a central lumen and at least one lumen circumferentially surrounding the central lumen;
   b) an energy-emitting source disposed within the central lumen of said catheter;
   c) a compression balloon surrounding the energy-emitting source within said catheter and having an inflated diameter that is greater than that of the bodily conduit in a relaxed state, the compression balloon including a proximal portion and a distal portion, the catheter including a plurality of inlet ports located near the proximal portion of the compression balloon and in fluid communication with the at least one lumen circumferentially surrounding the central lumen and a plurality of outlet ports spaced distally apart from the plurality of inlet ports and in fluid communication with the central lumen, the plurality of inlet ports and the plurality of outlet ports allowing fluid communication between the catheter and the compression balloon such that a circulating fluid can flow into the compression balloon via the plurality of inlet ports and out of the compression balloon and into the central lumen of the catheter via the plurality of outlet ports;
   d) anchoring means for positioning said energy-emitting source and said compression balloon adjacent the tissue to be treated;
   e) means for activating the energy-emitting source to radiate energy and to heat the tissue to be treated to greater than about 43° C.;

f) means for circulating fluid at a temperature in the range of approximately 30° C. to approximately 60° C. into the compression balloon surrounding the catheter to inflate the compression balloon to a sufficient pressure thereby maintaining the temperature of the bodily conduit and expanding the bodily conduit while the energy source is controlled to heat the tissue;

g) means for terminating the radiation of energy from the energy-emitting source upon completion of the time period to destroy diseased tissue; and h) means for maintaining the pressure of the compression balloon during and after thermotherapy.

2. The apparatus according to claim 1, wherein the catheter includes a flexible casing that defines the central lumen that receives the energy-emitting source and defines the at least one lumen circumferentially surrounding the central lumen.

3. The apparatus according to claim 1, further comprising an outflow restriction valve associated with the means for circulating fluid wherein the pressure of flow in the compression balloon is maintained approximately in the range of about 10-25 psi.

4. The apparatus according to claim 1, wherein the sufficient pressure is approximately 15 psi.

5. The apparatus according to claim 1, wherein the diameter of the catheter is less than about 22 French.

6. The apparatus according to claim 1, wherein the compression balloon is inflated to a diameter in the range of about 25-60 French.

7. The apparatus according to claim 1, wherein the compression balloon has a cylindrical shape.

8. The apparatus according to claim 7, wherein the compression balloon has a varying diameter along the length of the catheter.

9. The apparatus according to claim 8, wherein the ends of the compression balloon has a greater diameter than that of a middle region of the compression balloon.

10. The apparatus according to claim 7, wherein the compression balloon inflates so that it is asymmetric to the catheter.

11. The apparatus according to claim 1, wherein the bodily conduit is a urethra and the tissue to be treated is the prostate.

12. An apparatus for treatment of tissue within a body requiring thermotherapy, said apparatus comprising:
   a) a catheter including a shaft with a plurality of lumens, said catheter to be inserted into a bodily conduit;
   b) an energy-emitting source disposed within a central lumen of said catheter shaft;
   c) a compression balloon surrounding the energy-emitting source within said catheter shaft, the compression balloon including a proximal portion and a distal portion, the catheter including a plurality of inlet ports located near the proximal portion of the compression balloon and a plurality of outlet ports spaced distally apart from the plurality of inlet ports and in fluid communication with the central lumen of the catheter, the plurality of inlet ports and the plurality of outlet ports allowing fluid communication between the catheter and the compression balloon such that a circulating fluid can flow into the compression balloon via the plurality of inlet ports and out of the compression balloon and into the central lumen of the catheter via the plurality of outlet ports;
   d) anchoring means for positioning said energy-emitting source and said compression balloon adjacent the tissue to be treated;
   e) the location of the plurality of inlet ports and the location of the plurality of outlet ports allowing sufficient fluid flow and pressure to be maintained within the compression balloon thereby maintaining the temperature of the bodily conduit and expanding the bodily conduit while the energy source is controlled to heat the tissue;
   f) means for activating the energy-emitting source to radiate energy and to heat the tissue to be treated to greater than about 43° C.;
   g) means for terminating the radiation of energy from the energy-emitting source upon completion of the time period to destroy diseased tissue; and
   h) means for maintaining the pressure of the compression balloon during and after thermotherapy,
   i) wherein one of the catheter shaft and compression balloon has a shielding material applied thereto to define the heating pattern of the energy-emitting source.

13. The apparatus according to claim 12, further comprising means for longitudinally moving the energy-emitting source within the catheter so that the position of an emitting portion of the energy-emitting source can be varied to optimize heating of tissue.

14. An apparatus for treatment of tissue within a body requiring thermotherapy, said apparatus comprising:
   a) a catheter including a shaft with a plurality of lumens, the catheter configured to be inserted into a bodily conduit;
   b) an energy-emitting source disposed within a central lumen of the catheter shaft;
   c) a compression balloon surrounding the energy-emitting source within the catheter, the compression balloon including a distal portion and a proximal portion, the catheter including a plurality of inlet ports located near the proximal portion of the compression balloon and a plurality of outlet ports spaced distally apart from the plurality of inlet ports and in fluid communication with the central lumen of the catheter shaft, the plurality of inlet ports in fluid communication with at least one of the plurality of lumens allowing a circulating fluid to flow into the compression balloon via the plurality of inlet ports and out of the compression balloon and into the central lumen of the catheter shaft via the plurality of outlet ports; and
   d) an anchoring balloon for positioning the energy-emitting source and the compression balloon adjacent the tissue to be treated.

* * * * *